(12) United States Patent
Bocobachi Coronado

(10) Patent No.: US 11,566,137 B1
(45) Date of Patent: Jan. 31, 2023

(54) METHOD OF PRODUCING COSMETIC SKIN DYE

(71) Applicant: Armando Bocobachi Coronado, Phoenix, AZ (US)

(72) Inventor: Armando Bocobachi Coronado, Phoenix, AZ (US)

( * ) Notice: Subject to any disclaimer, the term of this patent is extended or adjusted under 35 U.S.C. 154(b) by 0 days.

(21) Appl. No.: 17/827,895

(22) Filed: May 30, 2022

(51) Int. Cl.
*C09B 61/00* (2006.01)
*A61Q 1/02* (2006.01)
*A61K 8/9789* (2017.01)

(52) U.S. Cl.
CPC ............ *C09B 61/00* (2013.01); *A61K 8/9789* (2017.08); *A61Q 1/02* (2013.01); *A61K 2800/805* (2013.01)

(58) Field of Classification Search
CPC .................. C09B 61/00; A61K 8/9789; A61K 2800/805; A61Q 1/02
USPC ............................................ 8/438, 440, 442
See application file for complete search history.

(56) References Cited

U.S. PATENT DOCUMENTS

| | | | | |
|---|---|---|---|---|
| 1,399,014 A * | 12/1921 | Hart | ......................... | C09B 61/00 8/438 |
| 4,132,793 A * | 1/1979 | Haber | ....................... | A23L 5/43 426/540 |
| 5,210,186 A * | 5/1993 | Mikalsen | ............... | C07C 403/24 536/127 |
| 6,406,503 B1 * | 6/2002 | Khatchatrian | .......... | C09B 61/00 8/526 |
| 6,582,730 B2 * | 6/2003 | Goswami | ................ | C09B 61/00 435/40.5 |
| 8,481,006 B2 | 7/2013 | Patnode | | |
| 10,130,572 B2 | 11/2018 | Adelson et al. | | |
| 2002/0187202 A1 * | 12/2002 | Goswami | ................ | C09B 61/00 424/520 |

FOREIGN PATENT DOCUMENTS

| | | | | |
|---|---|---|---|---|
| JP | 2002145732 A | * | 5/2002 | ............... A61K 7/00 |
| JP | 2007204423 A | * | 8/2007 | ........... A61K 36/899 |
| JP | 2008088098 A | * | 4/2008 | ........... A61K 36/899 |
| WO | WO 01/53418 A2 | * | 7/2001 | ............. C09B 61/00 |

* cited by examiner

*Primary Examiner* — Eisa B Elhilo
(74) *Attorney, Agent, or Firm* — Sanchelima & Associates, P.A.; Christian Sanchelima; Jesus Sanchelima

(57) ABSTRACT

A method of producing cosmetic skin dye, including a) extracting the liquid contained in the pecan husks, b) separating the extracted liquid in oil and sediments by means of natural sedimentation, c) homogeneously mixing said sediments with oil of the pecan husks to produce said skin dye, and d) applying the cosmetic skin dye in the skin of a user. The pecan husks are obtained from an unripe pecan. A higher concentration of sediments in the homogenous mixture produces a darker shade of cosmetic dye.

10 Claims, 1 Drawing Sheet

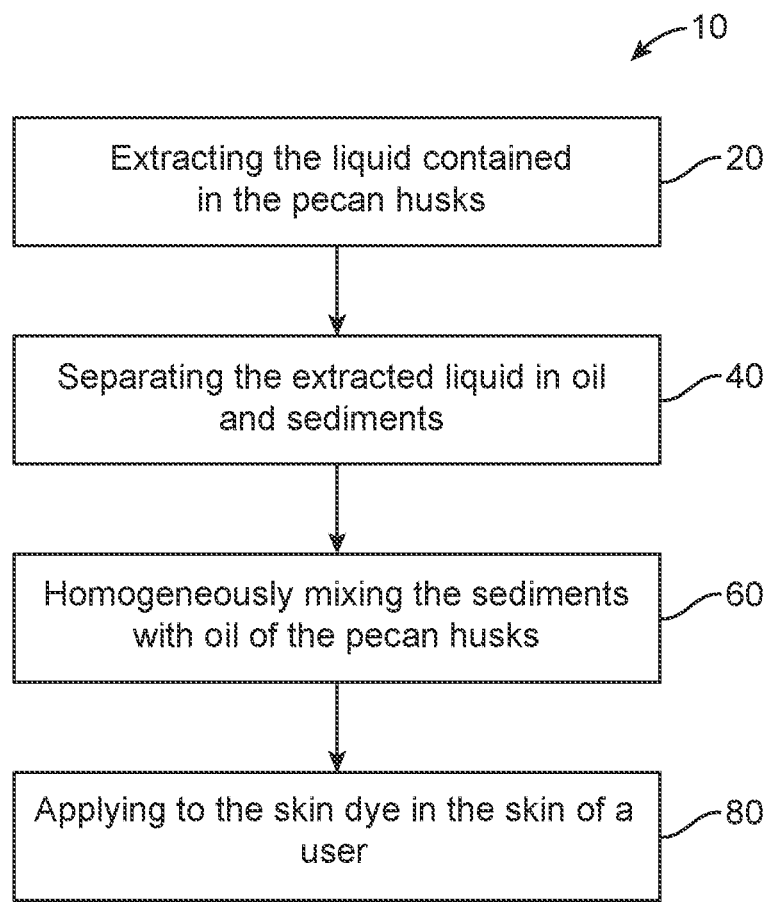

METHOD OF PRODUCING COSMETIC SKIN DYE

BACKGROUND OF THE INVENTION

1. Field of the Invention

The present invention relates to a method of producing cosmetic skin dye and, more particularly, to a method of producing cosmetic skin dye that uses pecan husks to create a cosmetic skin dye.

2. Description of the Related Art

Several designs for cosmetic skin dye have been designed in the past. None of them, however, include using the sediments to dye the skin of a person.

Applicant believes that a related reference corresponds to U.S. Pat. No. 8,481,006 issued for a topical composition for application to a user's skin that includes a bronzer that colors the user's skin. Applicant believes that another related reference corresponds to U.S. Pat. No. 10,130,572 issued for a method for concealing vitiligo that includes the use of brown liquids which have ingredients such as walnut extract. None of these references, however, teach of a method of producing cosmetic skin dye comprising extracting oils from pecan husks, filtering the oils to provide varying shade of sediments which is applied directly to the skin to dye the skin shades of brown.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a method of producing cosmetic skin dye which includes compacting the sediment to drain water thereof.

It is another object of this invention to provide a method of producing cosmetic skin dye that combines the pecan nuts sediment with a varied amount of pecan husks oils to produce pigment variations of the skin dye.

It is still another object of the present invention to provide a method of producing cosmetic skin dye which uses unripe pecan husks to produce a skin dye.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 represents a flow chart for a method 10 containing a first step 20, a second step 40, a third step 60 and a fourth step 80 in accordance with an embodiment of the present invention.

DETAILED DESCRIPTION OF THE EMBODIMENTS OF THE INVENTION

Referring now to the drawings, where the present invention is generally referred to with numeral 10, it can be observed that it basically includes a first step 20, a second step 40, a third step 60 and a fourth step 80. It should be understood there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

As best shown in FIG. 1, the first step 20 may include extracting the liquid contained in the pecan husks. It may be suitable to triturate the pecan husks to obtain the liquid from the pecan husks. The pecan husks may be separated from the pecan. In a preferred embodiment a juicer may be used to extract the liquid from the husks. The juicer may be a centrifugal force juicer, a masticating juicer, a twin gear juicer, a juicer press or any other juicer known in the prior art. It also may be suitable to use any other extraction method to extract the liquid from the pecan husks. The pecan husks may be husks of an unripe pecan. In a preferred embodiment the liquid from the husks is extracted before the husk breaks. The pecan is a species of hickory whose scientific name is *Carya illinoiensis*.

The second step 40 may include separating the extracted liquid in oil and sediments. It may be suitable to separate the oil to let the extracted liquid rest for a day. The extracted liquid may be separated in oil and sediments. The oil and the sediments may separate by density difference. The extracted oil may be in liquid phase. The sediments may be in a solid phase. It also may be suitable to use centrifugation to separate the sediment and the oil of the pecan husks or any other suitable method for phase separation. In a preferred embodiment, after sedimentation, the user may separate in different containers the oil and the sediments.

The third step 60 may be homogeneously mixing the sediments with oil of the pecan husks. Before mixing the sediments and the oil of the pecan husks it may be suitable to boil the sediments in water. For boiling the sediment water may be added to a container which contains the sediment. Adding the water and boiling the water may be used to remove impurities and oil left from the sediments. After boiling the sediments with water it may be suitable to compact the sediment to remove remaining water therein. It also may be suitable to use a dryer or an oven to remove any water left in the sediment. The sediment may be mixed with the previously extracted oil to create different shades of the skin dye. The sediments and the oil may be mixed until achieve a homogeneous mixture. It may be suitable to store the sediments in a desiccator for preventing gain humidity in the sediments.

A lower concentration of sediments in the homogeneous mixture of sediment with oil may be used to create lighter shades of skin dye. A higher concentration of sediments may be used to create darker shades of skin dye. It may be suitable to use a desiccator for preventing gain humidity in the homogeneous mixture. It also may be suitable to vacuum the homogeneous mixture to avoid spore formation. It may be suitable to add preservatives to the homogeneous mixture.

The fourth step 80 may include applying skin dye on the skin of a user. The homogeneous mixture is the skin dye. Before applying the homogeneous mixture, it may be suitable for the user to wash his face. The homogeneous mixture may be applied in circular movements in the outer part of the epidermis of a user. The homogeneous mixture may be applied as needed in the skin of the user. The skin absorption of the homogenous mixture may vary in accordance with the room temperature and the body temperature of the user, a higher temperature may allow a better absorption of the homogenous mixture.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A method of producing cosmetic skin dye, comprising:
   a) extracting the liquid contained in the pecan husks;
   b) separating the extracted liquid in oil and sediments;
   c) homogeneously mixing said sediments with oil of the pecan husks; and
   d) applying the cosmetic skin dye on the skin of a user.

2. The method for producing cosmetic skin dye set forth in claim 1, wherein said pecan husks are separated from a pecan nut.

3. The method for producing cosmetic skin dye set forth in claim 1, wherein said pecan husks are obtained of an unripe pecan.

4. The method for producing cosmetic skin dye set forth in claim 1, wherein an extractor is used for extracting said liquid contained in said pecan husks, said extractor is a juicer.

5. The method for producing cosmetic skin dye set forth in claim 1, wherein separation of liquid in oil and sediments is achieved by means of sedimentation.

6. The method for producing cosmetic skin dye set forth in claim 1, wherein said cosmetic skin dye is the homogeneous mixture.

7. The method for producing cosmetic skin dye set forth in claim 6, wherein higher concentration of sediments in said homogeneous mixture produces a darker shade of cosmetic dye.

8. The method for producing cosmetic skin dye set forth in claim 1, wherein said sediments are boiled in water before mixing said sediments with said oil to remove impurities in said sediment.

9. A method of producing cosmetic skin dye, comprising:
   a) extracting the liquid contained in the pecan husks, wherein said pecan husks are obtained from an unripe pecan, wherein said pecan is *Carya illinoinensis;*
   b) separating the extracted liquid in oil and sediments by means of natural sedimentation, wherein higher concentration of sediments in said homogenous mixture produces a darker shade of cosmetic dye;
   c) homogeneously mixing said sediments with oil of the pecan husks; and
   d) applying the cosmetic skin dye in the skin of a user, wherein said cosmetic skin dye is the homogenous mixture.

10. A method of producing cosmetic skin dye, comprising:
   a) extracting the liquid contained in the pecan husks by means of an extractor, wherein said pecan husks are obtained from an unripe pecan, said pecan is *Carya illinoinensis*, said extractor is a juicer extractor;
   b) separating the extracted liquid in oil and sediments by means of natural sedimentation;
   c) homogeneously mixing said sediments with oil of the pecan husks, wherein higher concentration of sediments in said homogenous mixture produces a darker shade of cosmetic dye, wherein said sediments are boiled in water before mixing said sediments with said oil to remove impurities in said sediment; and
   d) applying the cosmetic skin dye in the skin of a user, wherein said cosmetic skin dye is said homogeneous mixture.

* * * * *